US006797468B1

United States Patent
Scheu et al.

(10) Patent No.: US 6,797,468 B1
(45) Date of Patent: Sep. 28, 2004

(54) OLIGO NUCLEOTIDES METHOD AND KIT FOR DETECTING LISTERIA MONOCYTOGENES BY AMPLIFYING AND/ OR HYBRIDIZING NUCLEIC ACIDS

(75) Inventors: Pia Scheu, Berlin (DE); Alexander Gasch, Hochheim (DE); Kórnelia Berghof, Berlin (DE)

(73) Assignee: Biotecon Diagnostics GmbH, Berlin (DE)

( * ) Notice: Subject to any disclaimer, the term of this patent is extended or adjusted under 35 U.S.C. 154(b) by 0 days.

(21) Appl. No.: 09/786,011

(22) PCT Filed: Sep. 2, 1999

(86) PCT No.: PCT/EP99/06453

§ 371 (c)(1),
(2), (4) Date: Jun. 11, 2001

(87) PCT Pub. No.: WO00/14276

PCT Pub. Date: Mar. 16, 2000

(30) Foreign Application Priority Data

Sep. 2, 1998 (DE) .......................... 198 40 044

(51) Int. Cl.⁷ ........................... C12Q 1/68; C12P 19/34; C07H 21/04
(52) U.S. Cl. .......................... 435/6; 435/91.1; 435/91.2; 536/23.1; 536/24.3
(58) Field of Search .......................... 435/6, 91.1, 91.2; 536/23.1, 24.3

(56) References Cited

U.S. PATENT DOCUMENTS 5,474,796 A * 12/1995 Brennan .................... 427/2.13

FOREIGN PATENT DOCUMENTS

WO        WO 91/18997    * 12/1991    ................ 435/91.1

OTHER PUBLICATIONS

Accession No. Q20004, from geneseq database; 1991.*
Rossen et al, International Journal of Food Microbiology, vol. 14, pp 145–152; 1991.*
Domann et al; Infection and Immunity, vol. 59, pp 65–72; 1991.*
Ahern, Holly: The Scientist, pp 1–5; vol. 9, 1995.*
EST Accession No. AA207653, Mar. 1997; alignment provided.*

* cited by examiner

Primary Examiner—Jehanne Sitton
(74) Attorney, Agent, or Firm—Frommer Lawrence & Haug LLP; Ronald R. Santucci

(57) ABSTRACT

The present invention relates to a nucleic acid molecule or nucleic acid molecules and also to a method for the rapid and sensitive detection of bacteria of the pathogenic species *Listeria monocytogenes*. The invention further relates to a test kit or test kits for carrying out the detection methods mentioned.

2 Claims, No Drawings

OLIGO NUCLEOTIDES METHOD AND KIT FOR DETECTING LISTERIA MONOCYTOGENES BY AMPLIFYING AND/ OR HYBRIDIZING NUCLEIC ACIDS

The invention provides oligonucleotides, method and kit for detecting *Listeria monocytogenes* by nucleic acid amplification and/or nucleic acid hybridization.

The genus Listeria consists of the six species *L. monocytogenes, L. grayi L. innocua, L. ivanovii, L. seligeri* and *L. welshimeri*. Among these, only strains of the species *L. monocytogenes* are pathogenic for humans, in particular for those with a weakened immune system and for the elderly and the newborn. The most common symptoms of listeriosis are septicemia, meningitis and miscarriages. *L. monocytogenes* infections are caused especially by consuming contaminated food, in particular milk products, meat, poultry and vegetables.

A large number of methods for detecting *L. monocytogenes* are known. Conventional detection methods for *L. monocytogenes* comprise preconcentrating and subsequently isolating colonies on selection media (Lovett et al., J. Food Protection 50 (1987), 188–192; McClain & Lee, J. Assoc. Off. Anal. Chem. 71 (1988), 660–664). Single colonies are examined for their morphology or for biochemical or serological properties. An analysis may take up to 6–8 days.

Since especially readily perishable food is frequently contaminated with *L. monocytogenes*, various high-speed methods for detecting *L. monocytogenes* have been developed. Such methods are based either on immunological methods or on the application of nucleic acid probes.

In this connection, detection may be carried out by direct hybridization of probes to microbe-specific DNA or RNA (see, for example, Datta, A. R. et al., Appl. Environ. Microbiol. 53 (1987), 2256–2259). The disadvantage of those methods is the low sensitivity, since at least $10^5$–$10^6$ copies of the target nucleic acid are required. This can be compensated by combination with an amplification of the target sequence, for example using the polymerase chain reaction (PCR). A plurality of PCR methods for detecting *L. monocytogenes* have been described in the literature [for a review see, for example, Jones, D. D. & Bej, A. K. in "PCR Technology, Current Innovations", Griffin, H. G & Griffin, A. M., eds., (1994), 341–365]. See also U.S. Pat. Nos. 4,683,195; 4,683,202 and 4,965,188. Furthermore, the ligase chain reaction [WO publication 89/09835], "self-sustained sequence replication" [EP 329,822], "transcription based amplification system" [EP 310, 229] and Qβ RNA replicase system [U.S. Pat. No. 4,957,858] may be employed for the amplification of nucleic acids.

Some test kits for detection by means of antibodies are already commercially available. Most of these tests, however, display only low sensitivity and specificity.

To detect specific microorganisms by means of nucleic acid hybridization or nucleic acid amplification, microbe-specific oligonucleotides are commonly used whose base sequence is characteristic for the DNA or RNA of a specific microorganism or of a group of microorganisms. When using said microbe-specific oligonucleotides (for example as primers or probes) in connection with the methods mentioned above, hybridization to the DNA/RNA or amplification of DNA/RNA can occur under suitable reaction conditions only if the DNA/RNA of the particular microorganisms to be detected is present.

The detection methods described for *L. monocytogenes* are based mainly on those target genes which play a role in the pathogenicity of *L. monocytogenes*. It is known that some of these genes are located on the chromosome next to each other in a virulence gene cluster. Since the listeriolysin gene (hlyA) has been recognized first as to be clearly necessary for the pathogenicity of *L. monocytogenes* (Cossart, P. et al., Infect. Immun. 57 (1989), 3629–3636), most of the genotypic detection methods are based on this gene. The hlyA gene, however, is also found with high homology in nonpathogenic listeria (i.e. in *L. seeligeri* and *L. ivanovii*). In said detection methods, the appearance of false-positive results cannot be completely dismissed, since single point mutations in the region of the binding sites of primers or probes may already be sufficient for this.

It was possible to show that the metalloprotease gene (mpl) which is located in the genome right next to the hlyA gene is only present in *L. monocytogenes*, and thus not in nonpathogenic listeria (Domann, E. et al., Infect. Immun. 59 (1991), 65–72).

The suitability in principle of the DNA region flanking the hlyA gene for detecting *L. monocytogenes* by means of hybridization or amplification has been described (Rossen, L. et al., Int. J. Food Microbiol. 14 (1991), 145–152); however, no oligonucleotide sequences for such detection methods have been published yet.

The sequence of the *L. monocytogenes* mpl gene is described in the EMBL database under accession number X54619 [Domann, E. et al., Infect. Immnun. 59 (1991), 65–72]. Furthermore, parts of the sequence of the *L. monocytogenes* mpl gene are listed in the EMBL database under accession number X60035 [Rasmussen, O.F. et al., Infect. Immun. 59 (1991), 3945–3951].

It was an object of the present invention to develop a detection method which is suitable for routine use and in which the probability of false-positive results appearing is as low as possible for the particular user, even under very variable experimental conditions.

In particular, oligonucleotide sequences are to be provided which can be employed in a detection method for the *L. monocytogenes* metalloprotease gene (mpl).

These objects are achieved by providing nucleic acid molecules of the sequences (i) 5'-GAA AAA GCA TTT GAA GCC AT-3' or (ii) 5'-GCA ACT TCC GGC TCA GC-3' or (iii) 5'-TCG AAA AAG CAT TTG AAG CC-3' or (iv) 5'-GGT CAG AGT GAA GCT CAT GT-3' or (v) 5'-CTI TTC ACA TGA GCT TCA CTC TGA CCR A-3' or (vi) 5'-CTT TTT CTT TCA CTG GGT TTC CGA CAT-3 ' or (vii) 5'-GAT GAT TTC TTT TTC TTT CAC TGG ATT TCC AAT AT-3' or (viii) of the sequence complementary in each case to (i), (ii), (iii), (iv), (v), (vi), and (vii).

The oligonucleotides according to the invention may be defined as follows:

Oligonucleotide LM1: (sequence (i)=SEQ ID NO 1 corresponds to the position 2476 to 2495 of *L. monocytogenes* [according to Domann, E. et al. Infect. Immun. 59 (1991), 65–72).

Oligonucleotide LM 2: (sequence (ii)=SEQ ID NO 2) corresponds to the position 2608 to 2624 of *L. monocytogenes*.

Oligonucleotide LM3: (sequence (iii)=SEQ ID NO 3) corresponds to the position 2474 to 2493 of *L. monocytogenes*.

Oligonucleotide LM 4 (sequence (iv)=SEQ ID NO 4) corresponds to the position 2497 to 2516 of *L. monocytogenes*.

Oligonucleotide LMR 1: (sequence (v)=SEQ ID NO 5) corresponds to the position 2495 to 2522 of *L. monocytogenes*.

Oligonucleotide LMF 1: (sequence (vi)=SEQ ID NO 6) corresponds to the position 2525 to 2551 of *L. monocytogenes*.

Oligonucleotide LMF 2 (sequence (vii) SEQ ID NO 7) corresponds to the position 2525 to 2559 of *L. monocytogenes*.

In order to investigate the extent to which sequence variations of the mpl gene occur within the species *L. monocytogenes*, an internal fragment of 300 base pairs of 13 *L. monocytogenes* strains of various serovars (2 strains of the serovars 1/2a, 1 strain of the serovar 1/2b, 1 strain of the serovar 1/2c, 1 strain of the serovar 3a, 1 strain of the serovar 3b, 1 strain of the serovar 3c, 1 strain of the serovar 4a, 1 strain of the serovar 4a/b, 1 strain of the serovar 4b, 1 strain of the serovar 4c, 1 strain of the serovar 4d, and 1 strain of the serovar 7) was sequenced. On the basis of sequence comparisons, it was surprisingly found that the oligonucleotides LM1, LM 2, LM3, LM 4, LMF 1, LMF 2, LMR 1 and also sequences complementary thereto lead to highly specific detections in detection methods for *L. monocytogenes*. The preferred probes in this connection are the oligonucleotides LM4, LMR1, LMF1 and LMF2 and the sequences complementary thereto.

The invention in particular provides nucleic acid molecules which are characterized in that, with respect to at least 10 successive nucleotides of their nucleotide chain, they
(a) are identical to 10 successive nucleotides of the above nucleic acid molecules (i) to (viii) or
(b) match 9 out of 10 successive nucleotides of the above nucleic acid molecules (i) to (viii) or
(c) match 8 out of 10 successive nucleotides of the above nucleic acid molecules (i) to (viii) or
(d) are at least 90% homologous to a nucleic acid molecule according to claim 1.

The oligonucleotides of the invention may have a length usual for probes or primers, in particular for a PCR reaction, and further may have a length which can be produced by amplification, in particular by a PCR reaction, and preferably they may be from 10 to 250 bases and in particular from 15 to 30 bases in length.

They may be present in single-stranded or double-stranded form.

Thus, suitable microbe-specific oligonucleotides of the invention for detecting *L. monocytogenes* are nucleic acids, preferably from 10 to 250 bases and in particular from 15 to 30 bases in length, which match at least in a 10-base sequence the stated sequences LM 1, LM 2, LM 3, LM 4, LMF 1, LMF 2 and LMR 1 or the sequences complementary thereto. Relatively small deviations (1 to 2 bases) in this 10-base sequence are possible without the specificity stated in each case being lost during amplification and/or hybridization. It is known to the skilled worker that in the case of such relatively small deviations the reaction conditions have to be modified accordingly; cf., for example, T. Maniatis, Molecular Cloning, G. Sambrook & E. F. Fritsch, editors, Cold Spring Harbour [sic] Laboratory Press, 1989.

To detect *L. monocytogenes*, nucleic acids, preferably genomic DNA, are first released from cells contained in a sample or bacterial culture to be investigated. It is then possible, by means of nucleic acid hybridization and by using the microbe-specific oligonucleotides according to the invention as probe, directly to detect microbe-specific nucleic acid sequences in the sample to be investigated. Various methods known to the skilled worker are suitable for this purpose such as, for example, Southern blot or dot blot.

Especially because of the higher sensitivity, however, an indirect detection method is preferred in which the sought-after DNA/RNA sequences released as described above are first amplified by means of the abovementioned methods for amplifying nucleic acids, preferably PCR.

The primers employed for DNA/RNA amplification using the methods mentioned are the nucleic acid molecules according to the invention. In this connection, specific amplified molecules are formed only if *L. monocytogenes* DNA/RNA is present. A detection reaction (following or during the amplification reaction) using the nucleic acid molecules according to the invention as probes can increase the specificity of the detection method. In this detection reaction, oligonucleotides which are not entirely microbe-specific may likewise be used.

An alternative possibility is for the nucleic acid amplification to be carried out also in the presence of one or more not entirely specific oligonucleotides so that possibly DNA/RNA of other microorganisms not to be detected may also be amplified. An amplification method of this type is usually less specific and should therefore be safeguarded by a detection reaction (following or during the amplification reaction) using one or more of the nucleic acid molecule(s) according to the invention as probe(s).

According to the invention, it is possible to use various methods in order to detect the amplification products generated in the indirect methods. These include, inter alia, methods known per se such as visualization by means of gel electrophoresis, hybridization of probes to immobilized reaction products [coupled to nylon or nitrocellulose filters (Southern blots) or, for example, to beads or microtiter plates] and hybridization of the reaction products to immobilized probes (for example reverse dot blots or probes coupled to beads or microtiter plates). In addition, it is possible to use methods in which one or more of the nucleic acid molecules according to the invention can, as probes, qualitatively and quantitatively detect specifically forming amplification products during the PCR reaction ("online").

According to the invention, there is a large number of possibilities for the oligonucleotides according to the invention (e.g. probes and primers) to be possibly labeled or modified for the direct or indirect detection methods described. Thus, said oligonucleotides may contain, for example, radioactive, colored, fluorescent or otherwise modified or modifying groups, for example antibodies, antigens, enzymes or other substances with affinity to enzymes or enzyme complexes. Probes and primers may be either naturally occurring or synthetically produced double-stranded or single-stranded DNA or RNA or modified forms of DNA or RNA such as, for example, PNA (in these molecules the sugar units have been exchanged for amino acids or peptides). Individual or a plurality of nucleotides of the probes or primers according to the invention may have been replaced by analogous building blocks (such as, for example, nucleotides which are not naturally present in the target nucleic acid). In particular, up to 20% of at least 10 successive nucleotides of a nucleotide chain, in particular 1 or 2 nucleotides, may have been replaced by analogous building blocks known per se for probes and/or primers.

In the abovementioned indirect detection methods, detection may also involve an internally labeled amplified molecule. This may be carried out, for example, by incorporating modified nucleoside triphosphates (for example coupled to digoxigenin or fluorescein) during the amplification reaction.

The invention further provides a kit for analytical detection methods, in particular for detecting bacteria of the species *Listeria monocytogenes*, which kit contains one or more nucleic acid molecules according to the invention.

The nucleic acid molecules according to the invention or the appropriate kits may be used in a method for detecting the presence or absence of bacteria of the species *L. monocytogenes* in a sample, said method being preferably a nucleic acid hybridization and/or a nucleic acid amplification, such as a PCR. In this connection, bacteria to be detected can be distinguished from bacteria not to be detected on the basis of differences in the genomic DNA and/or RNA in at least one nucleotide position in the region of one of the nucleic acid molecules according to the invention.

EXAMPLE

Example 1

Detection of Bacteria of the Species *L. monocytogenes* using the Polymerase Chain Reaction DNA was isolated from pure cultures of the bacteria listed in table 1 by means of standard methods. In each case, approx. 10 to 100 ng of these DNA preparations were then introduced to the PCR in the presence of, in each case, 0.4 µM oligonucleotides LM 1 and LM 2, or LM 3 and LM 2, 200 µM dNTPs (Boehringer Mannheim), 2.5 mM MgCl$_2$, 16 mM (NH$_4$)$_2$SO$_4$, 67 mM, Tris/HCl (pH 8.8), 0.01% Tween 20 and 0.03 U/µl Taq DNA polymerase (Biomaster). The PCR was carried out in a Perkin Elmer 9600 Thermocycler using the temperature profile listed below:

| | | |
|---|---|---|
| Initial denaturation | 95° C. | 5 min |
| 35 cycles | 94° C. | 30 sec |
| | 57° C. | 30 sec |
| | 72° C. | 30 sec |
| Final synthesis | 72° C. | 5 min |

After finishing the PCR reaction, the amplification products were fractionated by means of agarose gel electrophoresis and visualized by ethidium bromide staining. The expected products of 149 bp and 151 bp in length, respectively, were observed only if DNA of strains of the species *L. monocytogenes* was present. The DNA fractionated in the gels was transferred to nylon filters by means of standard methods and hybridized with the 5' digoxigenin-labeled oligonucleotide LM 4 (sequence 4) in order to test the specificity. Hybridization was carried out in 5×SSC, 2% blocking reagent, 0.1% lauroylsarcosine, 0.02% SDS and 5 pmol/ml probe at 60° C. for 4 h. Washing was carried out using 2×SSC, 0.1% SDS for 2×10 mn at 60° C. Detection took place using standard methods by means of alkaline phosphatase conjugates (anti-digoxigenin-AP Fab fragment, Boehringer Mannheim) in the presence of 5-bromo-4-chloro-3-indolyl phosphate and 4-nitro blue tetrazolium chloride (Boehringer Mannheim).

On the filters, a band was observed only in those cases in which previously a band of 149 bp or 151 bp had been visible on the agarose gel. Thus, the presence of all of the 103 *L. monocytogenes* strains tested was detected by means of PCR and hybridization. In contrast, none of the bacterial strains tested which do not belong to said species were detected by this system.

TABLE 1

Results of PCR amplification using the oligonucleotides LM 1 and LM 2 (SEQ ID NO 1 and SEQ ID NO 2) and LM 3 and LM 2 (SEQ ID NO 3 and SEQ ID NO 2), respectively, and, in each case, subsequent hybridization using the oligonucleotide LM 4 (SEQ ID NO 4)

| Species | Serovar | Strain | LM1/LM2 | LM2/LM3 |
|---|---|---|---|---|
| Listeria welshimeri | | SLCC 767 | − | − |
| Listeria welshimeri | | SLCC 768 | − | − |
| Listeria welshimeri | | SLCC 5877 | − | − |
| Listeria welshimeri | | SLCC 5828 | − | − |
| Listeria welshimeri | | SLCC 6199 | − | − |
| Listeria welehimeri | | DSM 20650 | − | − |
| Listeria seeligeri | | SLCC 5921 | − | − |
| Listeria seeligeri | | SLCC 7303 | − | − |
| Listeria seeligeri | | SLCC 7309 | − | − |
| Listeria seeligeri | | SLCC 7329 | − | − |
| Listeria seeligeri | | SLCC 3954 | − | − |
| Listeria seeligeri | | DSM 20751 | − | − |
| Listeria innocua | | SLCC 5326 | − | − |
| Listeria innocua | | SLCC 7160 | − | − |
| Listeria innocua | | SLCC 7161 | − | − |
| Listeria innocua | | SLCC 7167 | − | − |
| Listeria innocua | | SLCC 7168 | − | − |
| Listeria innocua | | DSM 20649 | − | − |
| Listeria innocua | | SLCC 3408 | − | − |
| Listeria innocua | | NCTC 10528 | − | − |
| Listeria innocua | | SLCC 7139 | − | − |
| Listeria grayi | | DSM 20601 | − | − |
| Listeria grayi | | DSM 20596 | − | − |
| Listeria grayi | | SC 7308 | − | − |
| Listeria ivanovii | | DSM 20750 | − | − |
| Listeria ivanovii | | SLCC 2028 | − | − |
| Listeria ivanovii | | SLCC 2098 | − | − |
| Listeria ivanovii | | SLCC 2102 | − | − |
| Liateria ivanovii | | SLCC 2379 | − | − |
| Listeria ivanovii | | SLCC 4121 | − | − |
| Listeria ivanovii | | SLCC 4706 | − | − |
| Listeria ivanovii | | SLCC 4770 | − | − |
| Listeria ivanovii | | SLCC 5378 | − | − |
| Listeria ivanovii | | ATCC 19119 | − | − |
| L. monocytogenes | | ATCC 19111 | + | + |
| L. monocytogenes | | ATCC 19112 | + | + |
| L. monocytogenes | | ATCC 19113 | + | n.d. |
| L. monocytogenes | | ATCC 19114 | + | n.d. |
| L. monocytogenes | | ATCC 19115 | + | n.d. |
| L. monocytogenes | | ATCC 19116 | + | n.d. |
| L. monocytogenes | | ATCC 19117 | + | + |
| L. monocytogenes | | ATCC 19118 | + | n.d. |
| L. monocytogenes | | SLCC 53 | + | + |
| L. monocytogenes | | SLCC 2479 | + | + |
| L. monocytogenes | | SLCC 2482 | + | n.d. |
| L. monocytogenes | | SLCC 5835 | + | + |
| L. monocytogenes | 1/2 a | SLCC 4955 | + | + |
| L. monocytogenes | 1/2 a | SLCC 6204 | + | n.d. |
| L. monocytogenes | 1/2 a | SLCC 7149 | + | + |
| L. monocytogenes | 1/2 a | SLCC 7150 | + | + |
| L. monocytogenes | 1/2 a | SLCC 7153 | + | + |
| L. monocytogenes | 1/2 a | SLCC 7165 | + | n.d. |
| L. monocytogenes | 1/2 a | SLCC 7195 | + | n.d. |
| L. monocytogenes | 1/2 a | SLCC 7196 | + | n.d. |
| L. monocytogenes | 1/2 a | SLCC 7197 | + | n.d. |
| L. monocytogenes | 1/2 a | SLCC 7198 | + | n.d. |
| L. monocytogenes | 1/2 a | SLCC 7973 | + | n.d. |
| L. monocytogenes | 1/2 a | SLCC 7053 | + | n.d. |
| L. monocytogenes | 1/2 a | SLCC 7054 | + | n.d. |
| L. monocytogenes | 1/2 a | SLCC 7055 | + | n.d. |
| L. monocytogenes | 1/2 b | SLCC 6031 | + | n.d. |
| L. monocytogenes | 1/2 b | SLCC 7163 | + | + |
| L. monocytogenes | 1/2 b | SLCC 7151 | + | + |
| L. monocytogenes | 1/2 b | SLCC 7152 | + | n.d. |
| L. monocytogenes | 1/2 b | SLCC 7354 | + | + |
| L. monocytogenes | 1/2 b | SLCC 7367 | + | n.d. |
| L. monocytogenes | 1/2 b | SLCC 7059 | + | n.d. |
| L. monocytogenes | 1/2 c | SLCC 4950 | + | + |
| L. monocytogenes | 1/2 c | SLCC 6793 | + | + |
| L. monocytogenes | 1/2 c | SLCC 7154 | + | + |
| L. monocytogenes | 1/2 c | SLCC 7290 | + | n.d. |
| L. monocytogenes | 1/2 c | SLCC 7352 | + | n.d. |

TABLE 1-continued

Results of PCR amplification using the oligonucleotides LM 1 and LM 2 (SEQ ID NO 1 and SEQ ID NO 2) and LM 3 and LM 2 (SEQ ID NO 3 and SEQ ID NO 2), respectively, and, in each case, subsequent hybridization using the oligonucleotide LM 4 (SEQ ID NO 4)

| Species | Serovar | Strain | LM1/LM2 | LM2/LM3 |
|---|---|---|---|---|
| L. monocytogenes | 1/2 c | SLCC 7355 | + | n.d. |
| L. monocytogenes | 3 a | SLCC 4919 | + | + |
| L. monocytogenes | 3 a | SLCC 7135 | + | n.d. |
| L. monocytogenes | 3 a | SLCC 7179 | + | n.d. |
| L. monocytogenes | 3 b | SLCC 2540 | + | n.d. |
| L. monocytogenes | 3 b | SLCC 7140 | + | n.d. |
| L. monocytogenes | 3 b | SLCC 7381 | + | n.d. |
| L. monocytogenes | 3 c | SLCC 2471 | + | + |
| L. monocytogenes | 4 a | SLCC 5069 | + | + |
| L. monocytogenes | 4 a | SLCC 5070 | + | n.d. |
| L. monocytogenes | 4 a/b | SLCC 7083 | + | n.d. |
| L. monocytogenes | 4 a/b | SLCC 7065 | + | n.d. |
| L. monocytogenes | 4 a/b | SLCC 7069 | + | + |
| L. monocytogenes | 4 b | SLCC 4013 | + | + |
| L. monocytogenes | 4 b | SLCC 7194 | + | + |
| L. monocytogenes | 4 b | SLCC 7356 | + | + |
| L. monocytogenes | 4 b | SLCC 7370 | + | + |
| L. monocytogenes | 4 b | SLCC 7372 | + | + |
| L. monocytogenes | 4 b | SLCC 7373 | + | n.d. |
| L. monocytogenes | 4 b | SLCC 7374 | + | n.d. |
| L. monocytogenes | 4 b | SLCC 788 | + | n.d. |
| L. monocytogenes | 4 b | SLCC 7056 | + | n.d. |
| L. monocytogenes | 4 b | SLCC 7057 | + | n.d. |
| L. monocytogenes | 4 b | SLCC 7058 | + | n.d. |
| L. monocytogenes | 4 b | SLCC 7060 | + | n.d. |
| L. monocytogenes | 4 b | SLCC 7061 | + | n.d. |
| L. monocytogenes | 4 b | SLCC 7062 | + | n.d. |
| L. monocytogenes | 4 b | SLCC 7063 | + | n.d. |
| L. monocytogenes | 4 b | SLCC 7064 | + | n.d. |
| L. monocytogenes | 4 b | SLCC 7066 | + | n.d. |
| L. monocytogenes | 4 b | SLCC 7067 | + | n.d. |
| L. monocytogenes | 4 b | SLCC 7068 | + | n.d. |
| L. monocytogenes | 4 b | SLCC 7069 | + | n.d. |
| L. monocytogenes | 4 b | SLCC 7070 | + | n.d. |
| L. monocytogenes | 4 b | SLCC 7071 | + | n.d. |
| L. monocytogenes | 4 b | SLCC 7072 | + | n.d. |
| L. monocytogenes | 4 b | SLCC 7073 | + | n.d. |
| L. monocytogenes | 4 b | SLCC 7074 | + | n.d. |
| L. monocytogenes | 4 b | SLCC 7075 | + | n.d. |
| L. monocytogenes | 4 b | SLCC 7076 | + | n.d. |
| L. monocytogenes | 4 b | SLCC 7077 | + | n.d. |
| L. monocytogenes | 4 b | SLCC 7078 | + | n.d. |
| L. monocytogenes | 4 b | SLCC 7079 | + | n.d. |
| L. monocytogenes | 4 b | SLCC 7080 | + | n.d. |
| L. monocytogenes | 4 b | SLCC 7081 | + | n.d. |
| L. monocytogenes | 4 b | SLCC 7082 | + | n.d. |
| L. monocytogenes | 4 b | SLCC 7084 | + | n.d. |
| L. monocytogenes | 4 b | SLCC 7085 | + | n.d. |
| L. monocytogenes | 4 b | SLCC 7086 | + | n.d. |
| L. monocytogenes | 4 b | SLCC 7087 | + | n.d. |
| L. monocytogenes | 4 b | SLCC 7088 | + | n.d. |
| L. monocytogenes | 4 b | SLCC 7089 | + | n.d. |
| L. monocytogenes | 4 b | SLCC 7090 | + | n.d. |
| L. monocytogenes | 4 b | SLCC 7091 | + | n.d. |
| L. monocytogenes | 4 b | SLCC 7092 | + | n.d. |
| L. monocytogenes | 4 c | SLCC 4925 | + | n.d. |
| L. monocytogenes | 4 c | SLCC 4954 | + | + |
| L. monocytogenes | 4 c | SLCC 6277 | + | + |
| L. monocytogenes | 4 c | SLCC 6813 | + | + |
| L. monocytogenes | 4 c | SLCC 6821 | + | + |
| L. monocytogenes | 4 c | SLCC 6823 | + | + |
| L. monocytogenes | 4 d | SLCC 2375 | + | n.d. |
| L. monocytogenes | 4 d | SLCC 4926 | + | + |
| L. monocytogenes | 4 d | SLCC 4952 | + | + |
| L. monocytogenes | 7 | SLCC 2622 | + | + |
| Arthrobacter spec. | | DSM 312 | − | n.d. |
| Bacillus subtilis | | ATCC 6051 | − | − |
| Citrobacter freundii | | DSM 30040 | − | − |
| Citrobacter koseri | | DSM 4595 | − | n.d. |
| Clostridium bifermentans | | DSM 630 | − | n.d. |
| Clostridium aggrogenes | | IfGB 0303 | − | n.d. |
| Enterobacter agglomerans | | IfGB 0202 | − | n.d. |
| Enterobacter cloecae | | DSM 30054 | − | − |
| Enterabacter gergovia | | BC 674 | − | n.d. |
| Erwinia carotovora | | DSM 30168 | − | n.d. |
| Escherichia coli | | DSM 30083 | − | n.d. |
| Hafnia alvei | | IfGB 0101 | − | n.d. |
| Xlebaiella oxytaca | | DSM 5175 | − | n.d. |
| Xlebsiella pneumaniae | | DSM 2026 | − | n.d. |
| Lactobacillus spec. | | IfGB 1401 | − | n.d. |
| Lactob. bifermentans | | BC 8463 | − | − |
| Leuconostoc carnosum | | DSM 5576 | − | n.d. |
| Leucon. mesenteroides | | DSM 2146 | − | n.d |
| Micrococcus citreus | | IfGB 0601 | − | − |
| Micrococcus luteus | | DSM 348 | − | − |
| Pediococcus damnosus | | BC 505 | − | − |
| Proteus mirabilis | | IfGB 51 | − | − |
| Proteus vulgaris | | DSM 2041 | − | n.d. |
| Pseudomonas aeruginosa | | ATCC 10145 | − | n.d. |
| Pseudomonas fluorescens | | IfGB 0301 | − | − |
| Salmanella epec. | | BC 2426 | − | n.d. |
| Salmanella typhimurium | | BC 2157 | − | n.d. |
| Serratia marcescens | | BC 677 | − | − |
| Shigella flexneri | | DSM 4782 | − | n.d. |
| Staphylococcus aureus | | ATCC 6538 | − | − |
| Streptococcus faecallis | | DSM 20380 | − | n.d. |
| Strept. faecalis | | DSM 20478 | − | n.d. |
| Strept. diacetylactis | | BC 2149 | − | − |
| Strept. thermophilus | | DSM 20259 | − | n.d. |
| Yersinia enterocolitica | | DSM 4780 | − | n.d. |

IfGB: Institut für Gärungsgewerbe Berlin [Institute for Fermentation]
BC: BioteCon Strain Collection
SLCC: H.P.R. Seeliger Listeria Culture Collection, Würzburg, Germany
ATCC: American Type Culture Collection, Rockville, USA
DSM: Deutsche Sammlung von Microorganismen und Zellkulturen GmbH [German Collection of Microorganisms and Cell Cultures], Brunswick, Germany
n.d.: not done Example 2

Online Detection of Bacteria of the Species *L. monocytogenes* using the Polymerase Chain Reaction DNA was isolated from pure cultures of the strains and isolates listed in table 2 by means of standard methods. In each case, approx. 100 fg to 100 ng of said DNA preparations were then introduced to the PCR in the presence of, in each case, 0.4 μM oligonucleotide LM 1 and LM 2, 0.2 μM LMF 1 (label: 3'-fluorescein), LMF 2 (label: 3'-fluorescein) and LMR 1 (label: 5'-LC Red640 (Roche Diagnostics), 3'-phosphate), 200 μM dNTPs (Roche Diagnostics), 4 mM $MgCl_2$, 3 μg/μl BSA (Roche Diagnostics), 16 mM $(NH_4)_2SO_4$, 67 mM Tris/HCl (pH 8.8), 0.01% Tween 20 and 0.04 U/μl Taq DNA polymerase (HTB). The PCR was carried out in a Roche Diagnostics GmbH LightCycler using the temperature profile listed below:

| | | | |
|---|---|---|---|
| Initial denaturation | 95° C. | 2 min | |
| 42 cycles | 97° C. | 0 sec | |
| | 59° C. | 40 sec | |

During the PCR reaction, fluorescence signals (detection wavelength 640 nm) were only observed, if DNA of strains of the species L. monocytogenes was present.

TABLE 2

Results of PCR amplification using the oligonucleotides LM 1 and LM 2 (SEQ ID NO 1 and SEQ ID NO 2) and of, in each case, hybridization during the amplification reaction using the oligonucleotides LMF1, LMF2 and LMR1 (SEQ ID NO 5, SEQ ID NO 6, SEQ ID NO 7)

| Species | Serovar | Strain | LM1/LM2 LMF1/LMF2/LMR1 |
|---|---|---|---|
| Bacillus staeroth. | | DSM 456 | − |
| Staphylococcus aureus | | BC 197 | − |
| Escherichia coli (VTEC) | | BC 8318 | − |
| Clostridium perfringes | | BC 8799 | − |
| Leuconostoc mesent. | | DSM 20241 | − |
| Listeria welshimeri | | SLCC 767 | − |
| Listeria welshimeri | | SLCC 768 | − |
| Listeria welshimeri | | SLCC 5877 | − |
| Listeria seeligeri | | SLCC 5926 | − |
| Listeria seeligeri | | SLCC 7309 | − |
| Listeria innocua | | SLCC 5326 | − |
| Listeria innocua | | SLCC 7160 | − |
| Listeria innocua | | SLCC 7161 | − |
| Listeria grayi | | DSM 20601 | − |
| Listeria ivanovii | | SLCC 2028 | − |
| Listeria ivanovii | | SLCC 2098 | − |
| Listeria ivanovii | | SLCC 2102 | − |
| L. monocytogenes | 1/2 a | SLCC 4955 | + |
| L. monocytogenes | 1/2 a | SLCC 6204 | + |
| L. monocytogenes | 1/2 a | SLCC 7149 | + |
| L. monocytogenes | 1/2 a | SLCC 7150 | + |
| L. monocytogenes | 1/2 a | SLCC 7153 | + |
| L. monocytogenes | 1/2 b | SLCC 7151 | + |
| L. monocytogenes | 1/2 b | SLCC 7152 | + |
| L. monocytogenes | 1/2 b | SLCC 7354 | + |
| L. monocytogenes | 1/2 b | SLCC 7367 | + |
| L. monocytogenes | 1/2 b | SLCC 7059 | + |
| L. monocytogenes | 1/2 c | SLCC 6793 | + |
| L. monocytogenes | 1/2 c | SLCC 7154 | + |
| L. monocytogenes | 1/2 c | SLCC 7290 | + |
| L. monocytogenes | 1/2 c | SLCC 7352 | + |

TABLE 2-continued

Results of PCR amplification using the oligonucleotides LM 1 and LM 2 (SEQ ID NO 1 and SEQ ID NO 2) and of, in each case, hybridization during the amplification reaction using the oligonucleotides LMF1, LMF2 and LMR1 (SEQ ID NO 5, SEQ ID NO 6, SEQ ID NO 7)

| Species | Serovar | Strain | LM1/LM2 LMF1/LMF2/LMR1 |
|---|---|---|---|
| L. monocytogenes | 1/2 c | SLCC 7355 | + |
| L. monocytogenes | 3 a | SLCC 4949 | + |
| L. monocytogenes | 3 a | SLCC 7135 | + |
| L. monocytogenes | 3 a | SLCC 7179 | + |
| L. monocytogenes | 3 b | SLCC 7140 | + |
| L. monocytogenes | 3 b | SLCC 7381 | + |
| L. monocytogenes | 3 c | SLCC 2471 | + |
| L. monocytogenes | 4 a | SLCC 5069 | + |
| L. monocytogenes | 4 a | SLCC 5070 | + |
| L. monocytogenes | 4 a/b | SLCC 7083 | + |
| L. monocytogenes | 4 a/b | SLCC 7065 | + |
| L. monocytogenes | 4 a/b | SLCC 7069 | + |
| L. monocytogenes | 4 b | SLCC 4013 | + |
| L. monocytogenes | 4 b | SLCC 7194 | + |
| L. monocytogenes | 4 b | SLCC 7356 | + |
| L. monocytogenes | 4 b | SLCC 7370 | + |
| L. monocytogenes | 4 b | SLCC 7372 | + |
| L. monocytogenes | 4 c | SLCC 4925 | + |
| L. monocytogenes | 4 c | SLCC 4954 | + |
| L. monocytogenes | 4 c | SLCC 6277 | + |
| L. monocytogenes | 4 c | SLCC 6813 | + |
| L. monocytogenes | 4 c | SLCC 6821 | + |
| L. monocytogenes | 4 d | SLCC 2375 | + |
| L. monocytogenes | 4 d | SLCC 4926 | + |
| L. monocytogenes | 4 d | SLCC 4952 | + |
| L. monocytogenes | 7 | SLCC 2622 | + |

IfGB: Institut für Gärungsgewerbe Berlin [Institute for Fermentation]
BC: BioteCon Strain Collection
SLCC: H.P.R. Seeliger Listeria Culture Collection, Würzburg, Germany
ATCC: American Type Culture Collection, Rockville, USA
DSM: Deutsche Sammlung von Microorganismen und Zellkulturen GmbH [German Collection of Microorganisms and Cell Cultures], Brunswick, Germany

What is claimed is:

1. An isolated nucleic acid molecule selected from the group consisting of
   a) SEQ ID NO 1 5'-GAA AAA GCA TTT GAA GCC AT-3' or
   b) SEQ ID NO 2 5'-GCA ACT TCC GGC TCA GC-3' or
   c) SEQ ID NO 3 5'-TCG AAA AAG CAT TTG AAG CC-3' or
   d) SEQ ID NO 4 5'-GGT CAG AGT GAA GCT CAT GT-3' or
   e) SEQ ID NO 5 5'-CTI TTC ACA TGA GCT TCA CTC TGA CCR A-3' or
   f) SEQ ID NO 6 5'-CTT TTT CTT TCA CTG GGT TTC CGA CAT-3' or
   g) SEQ ID NO 7 5'-GAT GAT TTC TTT TTC TTT CAC TGG ATT TCC AAT AT-3' and
   h) the sequence completely complementary to a), b), c), d), e), f) or g).

2. A method for specifically detecting DNA of the bacterial species *Listeria monocytogenes* in a test sample without cross-reactivity with DNA from other bacterial species, comprising the steps of:
   (i) providing a test sample containing bacterial genomic DNA;
   (ii) providing at least one nucleic acid molecule of claim 1 for use as either a primer for a PCR reaction or a probe for a hybridisation reaction; and
   performing either a PCR reaction or a hybridization reaction on said bacterial genomic DNA using said primer or probe, whereby a positive PCR result or a positive hybridisation result indicates that the test sample contains DNA of the bacterial species *Listeria monocytogenes*.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Listeria monocytogenes

<400> SEQUENCE: 1
gaaaaagcat ttgaagccat                                          20

<210> SEQ ID NO 2
<211> LENGTH: 17
<212> TYPE: DNA
<213> ORGANISM: Listeria monocytogenes

<400> SEQUENCE: 2

```
                                          -continued gcaacttccg gctcagc                                                                    17

<210> SEQ ID NO 3
<211> LENGTH: 20
<212> TYPE: DNA
<213> ORGANISM: Listeria monocytogenes

<400> SEQUENCE: 3
tcgaaaaagc atttgaagcc                                                                 20

<210> SEQ ID NO 4
<211> LENGTH: 20
<212> TYPE: DNA
<213> ORGANISM: Listeria monocytogenes

<400> SEQUENCE: 4
ggtcagagtg aagctcatgt                                                                 20

<210> SEQ ID NO 5
<211> LENGTH: 28
<212> TYPE: DNA
<213> ORGANISM: Listeria monocytogenes
<220> FEATURE:
<221> NAME/KEY: misc_difference
<222> LOCATION: (3)
<223> OTHER INFORMATION: n=i

<400> SEQUENCE: 5
ctnttcacat gagcttcact ctgaccra                                                        28

<210> SEQ ID NO 6
<211> LENGTH: 27
<212> TYPE: DNA
<213> ORGANISM: Listeria monocytogenes

<400> SEQUENCE: 6
cttttctttt cactgggttt ccgacat                                                         27

<210> SEQ ID NO 7
<211> LENGTH: 35
<212> TYPE: DNA
<213> ORGANISM: Listeria monocytogenes

<400> SEQUENCE: 7
gatgatttct ttttctttca ctggatttcc aatat                                                35
```